US011944960B2

(12) United States Patent
Tsai et al.

(10) Patent No.: US 11,944,960 B2
(45) Date of Patent: Apr. 2, 2024

(54) METHOD FOR FABRICATING NICKEL-CERIUM DIOXIDE-ALUMINUM OXIDE HYBRID NANOPARTICLE CLUSTER CATALYST, NICKEL-CERIUM DIOXIDE-ALUMINUM OXIDE HYBRID NANOPARTICLE CLUSTER CATALYST AND METHOD FOR SYNTHESIZING POLYETHERAMINE

(71) Applicants: NATIONAL TSING HUA UNIVERSITY, Hsinchu (TW); Chang Chun Plastics Co., Ltd., Taipei (TW); Chang Chun Petrochemical Co., LTD., Taipei (TW); DAIREN CHEMICAL CORP., Taipei (TW)

(72) Inventors: De-Hao Tsai, Zhubei (TW); Hung-Yen Chang, Taoyuan (TW); Guan-Hung Lai, Yunlin County (TW)

(73) Assignees: NATIONAL TSING HUA UNIVERSITY, Hsinchu (TW); Chang Chun Plastics Co., Ltd., Taipei (TW); Chang Chun Petrochemical Co., LTD., Taipei (TW); DAIREN CHEMICAL CORP., Taipei (TW)

( * ) Notice: Subject to any disclaimer, the term of this patent is extended or adjusted under 35 U.S.C. 154(b) by 1014 days.

(21) Appl. No.: 16/858,434

(22) Filed: Apr. 24, 2020

(65) Prior Publication Data
US 2021/0154655 A1 May 27, 2021

(30) Foreign Application Priority Data
Nov. 25, 2019 (TW) .................................. 108142784

(51) Int. Cl.
B01J 37/02 (2006.01)
B01J 6/00 (2006.01)
(Continued)

(52) U.S. Cl.
CPC ........... *B01J 37/0221* (2013.01); *B01J 6/001* (2013.01); *B01J 23/755* (2013.01); *B01J 35/40* (2024.01);
(Continued)

(58) Field of Classification Search
None
See application file for complete search history.

(56) References Cited

U.S. PATENT DOCUMENTS

2005/0112056 A1* 5/2005 Hampden-Smith ........................ B01J 20/3433
502/415

FOREIGN PATENT DOCUMENTS

TW 201924779 A 7/2019
TW 201938521 A 10/2019
(Continued)

OTHER PUBLICATIONS

Machine translation of TW201924779A (Tsai) (Year: 2019).*
(Continued)

Primary Examiner — Melissa S Swain
Assistant Examiner — Keling Zhang
(74) Attorney, Agent, or Firm — Joseph C. Zucchero; Carolyn S. Elmore; Elmore Patent Law Group

(57) ABSTRACT

The present disclosure provides a method for fabricating a nickel-cerium dioxide-aluminum oxide hybrid nanoparticle cluster catalyst. The method includes a solution preparation step, an aerosolizing step, a drying step, a first calcining step, a reducing gas adding step, and a second calcining step. The solution preparation step is provided for preparing a precursor solution. The aerosolizing step is performed for obtaining an atomized droplet. The drying step is performed for converting to a precursor crystallite. The first calcining step is performed for obtaining an oxidation state catalyst. The
(Continued)

reducing gas adding step is performed for adding hydrogen. The second calcining step is performed for obtaining the nickel-cerium dioxide-aluminum oxide hybrid nanoparticle cluster catalyst.

**8 Claims, 11 Drawing Sheets
(2 of 11 Drawing Sheet(s) Filed in Color)**

(51) Int. Cl.
    *B01J 23/755*     (2006.01)
    *B01J 35/40*     (2024.01)
    *B01J 37/16*     (2006.01)
    *C07C 213/02*     (2006.01)
    *C07C 217/42*     (2006.01)

(52) U.S. Cl.
    CPC ............. *B01J 37/16* (2013.01); *C07C 213/02* (2013.01); *C07C 217/42* (2013.01); *C07C 2523/755* (2013.01)

(56) References Cited

FOREIGN PATENT DOCUMENTS

TW     1677374 B     11/2019
WO     WO-2018032522 A1 *   2/2018  ............. B01J 21/04

OTHER PUBLICATIONS

Iriondo et al., Glycerol steam reforming over Ni catalysts supported on ceria and ceria-promoted alumina, International Journal of Hydrogen Energy, 2010, 35, 11622-11633 (Year: 2010).*
Rozita et al., A study of commercial nanparticulate y-Al2O3 catalyst support, ChemCatChem, 2013, 2695-2706 (Year: 2013).*
Machine translation of Ren et al., WO 2018032522A1 (Ren) (Year: 2018).*

* cited by examiner

100

- 110 a solution preparation step is performed
- 120 an aerosolizing step is performed
- 130 a drying step is performed
- 140 a first calcining step is performed
- 150 a reducing gas adding step is performed
- 160 a second calcining step is performed

Fig. 1

200 a nickel-cerium dioxide-aluminum oxide hybrid nanoparticle cluster catalyst is provided — 210 a reductive amination reaction of polypropylene glycol step is performed — 220

METHOD FOR FABRICATING NICKEL-CERIUM DIOXIDE-ALUMINUM OXIDE HYBRID NANOPARTICLE CLUSTER CATALYST, NICKEL-CERIUM DIOXIDE-ALUMINUM OXIDE HYBRID NANOPARTICLE CLUSTER CATALYST AND METHOD FOR SYNTHESIZING POLYETHERAMINE

RELATED APPLICATION

This application claims priority to Taiwan Application Serial Number 108142784, filed Nov. 25, 2019, which is herein incorporated by reference.

BACKGROUND

Technical Field

The present disclosure relates to a method for fabricating catalysts. More particularly, the present disclosure relates to a method for fabricating a nickel-cerium dioxide-aluminum oxide hybrid nanoparticle cluster catalyst, a nickel-cerium dioxide-aluminum oxide hybrid nanoparticle cluster catalyst thereof and a method for synthesizing polyetheramine.

Description of Related Art

Polyetheramines (PEA) are the important chemical raw materials and extensively used as intermediates for the production of petrochemicals, such as household chemicals, pesticides and pharmaceuticals. The reductive amination reaction of polypropylene glycol (PPG) is catalyzed by the heterogeneous catalysts so as to produce polyetheramines with the desired selectivity recognized as one of the effective production routes.

However, heterogeneous catalysts are generally prepared in the form of solution. The size and shape of the catalyst are limited by the physical or chemical properties of the solvent, such as solubility, boiling point, etc., or other additives, such as surfactant, are used in the solvent to make the catalyst form an undesired size and shape. Especially, the nanostructured catalyst material has a greater impact.

Therefore, how to prepare the composite heterogeneous catalysts and adjust the formulation thereof to improve the catalytic activity of the catalyst material, and the stability of the material and the reaction under the high temperature and pressure, is the goal of the relevant industry.

SUMMARY

According to one aspect of the present disclosure, a method for fabricating a nickel-cerium dioxide-aluminum oxide hybrid nanoparticle cluster catalyst includes steps as follows. A solution preparation step is performed, wherein a catalytically active precursor and a supporter precursor are mixed to obtain a precursor solution, and the catalytically active precursor contains a nickel ion and a cerium ion, the supporter precursor contains an aluminum ion. An aerosolizing step is performed, wherein the precursor solution is aerosolized to obtain an atomized droplet. A drying step is performed, wherein the atomized droplet is converted to a precursor crystallite by evaporation-induced self-assembly. A first calcining step is performed, wherein the precursor crystallite is calcined to obtain an oxidation state catalyst. A reducing gas adding step is performed, wherein hydrogen is added as a reducing gas. A second calcining step is performed, wherein the oxidation state catalyst is calcined to obtain the nickel-cerium dioxide-aluminum oxide hybrid nanoparticle cluster catalyst.

According to another aspect of the present disclosure, a nickel-cerium dioxide-aluminum oxide hybrid nanoparticle cluster catalyst is provided. The nickel-cerium dioxide-aluminum oxide hybrid nanoparticle cluster catalyst is fabricated by the method according to the aforementioned aspect.

According to further another aspect of the present disclosure, a method for synthesizing polyetheramine includes steps as follows. A nickel-cerium dioxide-aluminum oxide hybrid nanoparticle cluster catalyst is provided, wherein the nickel-cerium dioxide-aluminum oxide hybrid nanoparticle cluster catalyst is fabricated by the method according to the aforementioned aspect. A reductive amination reaction of polypropylene glycol step is performed, wherein polypropylene glycol is performed the reductive amination reaction by using the nickel-cerium dioxide-aluminum oxide hybrid nanoparticle cluster catalyst as a catalyst, so as to obtain polyetheramine at an environment contained hydrogen and ammonia.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiment, with reference made to the accompanying drawings as follows:

FIG. 1 is a flow chart of a method for fabricating a nickel-cerium dioxide-aluminum oxide hybrid nanoparticle cluster catalyst according to one embodiment of the present disclosure.

FIG. 2 is a flow chart of a method for synthesizing polyetheramine according to another embodiment of the present disclosure.

DETAILED DESCRIPTION

Figure 3A:
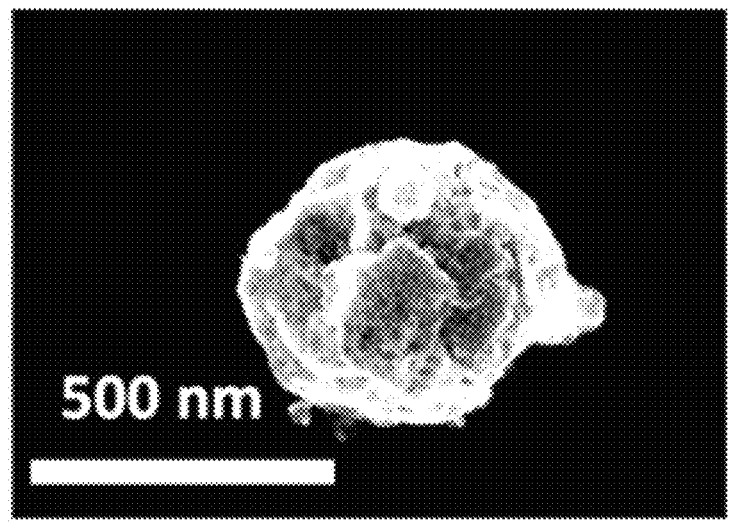
FIG. 3A is a FESEM image of Comparative Example 1.

The present disclosure will be further exemplified by the following specific embodiments. However, the embodiments can be applied to various inventive concepts and can be embodied in various specific ranges. The specific embodiments are only for the purposes of description, and are not limited to these practical details thereof.

Please refer to FIG. 1, which is a flow chart of a method for fabricating a nickel-cerium dioxide-aluminum oxide hybrid nanoparticle cluster catalyst 100 according to one embodiment of the present disclosure. It should be noted that the method for fabricating the nickel-cerium dioxide-aluminum oxide hybrid nanoparticle cluster catalyst is mainly prepared by an aerosol process, and the aerosol process can improve the limitations of physical or chemical caused by the solvent properties. The method for fabricating the nickel-cerium dioxide-aluminum oxide hybrid nanoparticle cluster catalyst 100 includes a step 110, a step 120, a step 130, a step 140, a step 150 and a step 160.

In the step 110, a solution preparation step is performed, wherein a catalytically active precursor and a supporter precursor are mixed to obtain a precursor solution. The catalytically active precursor contains a nickel ion and a cerium ion, and the supporter precursor contains an aluminum ion. Specifically, in the present disclosure, the catalytically active precursor can be but not limited to a mixed solution of nickel nitrate ($Ni(NO_3)_2 \cdot 6H_2O$) and cerium nitrate ($Ce(NO_3)_3 \cdot 6H_2O$), and the supporter precursor can be aluminum oxide nanopowder. Furthermore, in the precursor solution, an atomic ratio of cerium to nickel can be but not limited to 0.5 to 0.8, preferably can be 0.61, and an atomic ratio of aluminum to nickel can be but not limited to 0.3 to 1.8. Next, the supporter precursor is dissolved in water, and then mixed with the catalytically active precursor. The above mixed solution is adjusted pH value to 2.5 to 4 using glacial acetic acid or nitric acid. Preferably the pH value can be adjusted to 3, so that aluminum oxide can be stably dispersed in the solution to form the precursor solution.

In the step 120, an aerosolizing step is performed, wherein the precursor solution is aerosolized to obtain an atomized droplet. Specifically, in the present disclosure, a customized nebulizer can be used, and adding compressed nitrogen to convert the precursor solution into the atomized droplet at a flow rate of 1.5 L/min, but is not limited to the disclosure.

In the step 130, a drying step is performed, wherein the atomized droplet is converted to a precursor crystallite by evaporation-induced self-assembly. Specifically, in the present disclosure, a drying unit composed of a flow preheater and a diffusion dryer can be used to remove water in the atomized droplet. Furthermore, in the drying step, the dried catalytically active precursor and the supporter precursor are formed a dried and uniformly distributed precursor crystallite by the rapidly evaporation-induced self-assembly.

In the step 140, a first calcining step is performed, wherein the precursor crystallite is calcined to obtain an oxidation state catalyst, and a temperature of the first calcining step can range from 400° C. to 700° C. Specifically, in the present disclosure, the first calcining step can be performed in a first flow reactor. The first flow reactor is disposed in a first tube furnace, wherein the operating temperature of the first tube furnace is 400° C. to 700° C. In the first flow reactor, the precursor crystallite is thermally decomposed into the oxidation state catalyst. At this time, nickel oxide and cerium dioxide are uniformly dispersed on the surface of the aluminum oxide nanoparticle cluster.

In the step 150, a reducing gas adding step is performed, wherein hydrogen is added as a reducing gas, and the hydrogen flow rate can be 250 mL/min.

In the step 160, a second calcining step is performed, wherein the oxidation state catalyst is calcined to obtain the nickel-cerium dioxide-aluminum oxide hybrid nanoparticle cluster catalyst, and a temperature of the second calcining step can range from 600° C. to 800° C. Specifically, in the present disclosure, the second calcining step can be performed in a second flow reactor. The second flow reactor is disposed in a second tube furnace, wherein the operating temperature of the second tube furnace is 600° C. to 800° C. The oxidation state catalyst is sent to the second flow reactor under the hydrogen atmosphere, and nickel oxide is reduced to nickel selectively to obtain the nickel-cerium dioxide-aluminum oxide hybrid nanoparticle cluster catalyst.

Therefore, the present disclosure further provides the nickel-cerium dioxide-aluminum oxide hybrid nanoparticle cluster catalyst fabricated by the aforementioned method, which can be used to catalyze the reductive amination reaction of polypropylene glycol to synthesize polyetheramine. Hereafter, a method for synthesizing polyetheramine 200 using the aforementioned nickel-cerium dioxide-aluminum oxide hybrid nanoparticle cluster catalyst will be further described with FIG. 2. The method for synthesizing polyetheramine 200 includes a step 210 and a step 220.

In the step 210, the nickel-cerium dioxide-aluminum oxide hybrid nanoparticle cluster catalyst is provided. Then, in the step 220, a reductive amination reaction of polypropylene glycol step is performed, wherein polypropylene glycol is performed the reductive amination reaction by the aforementioned nickel-cerium dioxide-aluminum oxide hybrid nanoparticle cluster catalyst used as the catalyst, so as to obtain polyetheramine at an environment contained hydrogen and ammonia. A molar ratio of hydrogen ($H_2$) to polypropylene glycol (PPG) can be range from 1 to 1.55, and a molar ratio of ammonia ($NH_3$) to polypropylene glycol (PPG) can be range from 38 to 40.6. The details of the step 220 will be described in the subsequent embodiments, and will not be described herein.

Hereinafter, the specific examples and the comparative examples are described to explain the detail of the nickel-cerium dioxide-aluminum oxide hybrid nanoparticle cluster catalyst, the preparation method thereof, and the method for synthesizing polyetheramine thereof used to achieve the effects which are provided in the present disclosure.

Example

1. Preparation and Material Properties Analysis of a Nickel-Cerium Dioxide-Aluminum Oxide Hybrid Nanoparticle Cluster Catalyst A nickel-cerium dioxide-aluminum oxide hybrid nanoparticle cluster catalyst of the present disclosure is prepared by a step 110 to a step 160 of a method for fabricating a nickel-cerium dioxide-aluminum oxide hybrid nanoparticle cluster catalyst 100 of FIG. 1. First, nickel nitrate, cerium nitrate, and aluminum oxide powder are used as the raw materials of nickel, cerium dioxide and aluminum oxide, respectively. Then, nickel nitrate, cerium nitrate, and aluminum oxide powder are mixed and dissolved in water, and the pH value is adjusted to 3 by glacial acetic acid to form the precursor solution.

Next, the customized nebulizer is used, and adding compressed nitrogen to convert the precursor solution into the atomized droplet at the flow rate of 1.5 L/min. The drying unit composed of the flow preheater and the diffusion dryer filled with granular silica gel can be used to remove water in the atomized droplet by evaporation-induced self-assembly to obtain the dried precursor crystallite. Then, the precursor crystallite is sent to the first flow reactor, and the gas phase thermal decomposition is performed at 500° C. for 4 seconds to decompose the precursor crystallite into the oxidation state catalyst. Finally, the oxidation state catalyst is sent to the second flow reactor under the hydrogen environment, and selective thermal reduction is performed at 800° C. for 13 seconds to reduce nickel oxide to nickel, so as to obtain the nickel-cerium dioxide-aluminum oxide hybrid nanoparticle cluster catalyst.

The nickel-cerium dioxide-aluminum oxide hybrid nanoparticle cluster catalyst of the present disclosure can be controlled the crystallite size of the active metal and the metal surface area by controlling the composition concentration to achieve the high catalytic activity, the selectivity and the stability of the nickel-cerium dioxide-aluminum oxide hybrid nanoparticle cluster catalyst. The crystallite size of the nickel-cerium dioxide-aluminum oxide hybrid nanoparticle cluster catalyst is analyzed by using the X-ray diffraction (XRD). The morphology and the element distribution of the nickel-cerium dioxide-aluminum oxide hybrid nanoparticle cluster catalyst are analyzed by using the field emission scanning electron microscope (FESEM) and energy dispersive X-ray spectrometer (EDS). The specific surface area, the metal surface area and the metal dispersion of the nickel-cerium dioxide-aluminum oxide hybrid nanoparticle cluster catalyst are analyzed by using the specific surface area and porosity analyzer and the chemisorption analyzer. The activity test, the selectivity test and the stability test are performed by the aforementioned analysis.

The controlling conditions of Example 1 to Example 2 and Comparative Example 1 to Comparative Example 4 are shown in Table 1, wherein $C_{Ni}$, $C_{Ce}$, $C_{Al}$ represent the concentrations of Ni, $CeO_2$ and $Al_2O_3$ in the precursor solution, respectively. Furthermore, the concentration of each element can also be used to describe the atomic ratio thereof.

TABLE 1

|  | $C_{Ni}$ (wt %) | $C_{Ce}$ (wt %) | $C_{Al}$ (wt %) | $C_{Ce}/C_{Ni}$ | $C_{Al}/C_{Ni}$ |
| --- | --- | --- | --- | --- | --- |
| Example 1 | 31.5 | 19.3 | 49.1 | 0.61 | 1.56 |
| Example 2 | 52.0 | 31.8 | 16.2 | 0.61 | 0.31 |
| Comparative Example 1 | 62.0 | 38.0 | 0 | 0.61 | 0 |
| Comparative Example 2 | 76.2 | 0 | 23.8 | 0 | 0.31 |
| Comparative Example 3 | 100 | 0 | 0 | 0 | 0 |
| Comparative Example 4 | 0 | 0 | 100 | N/A | N/A |

Figure 3B:
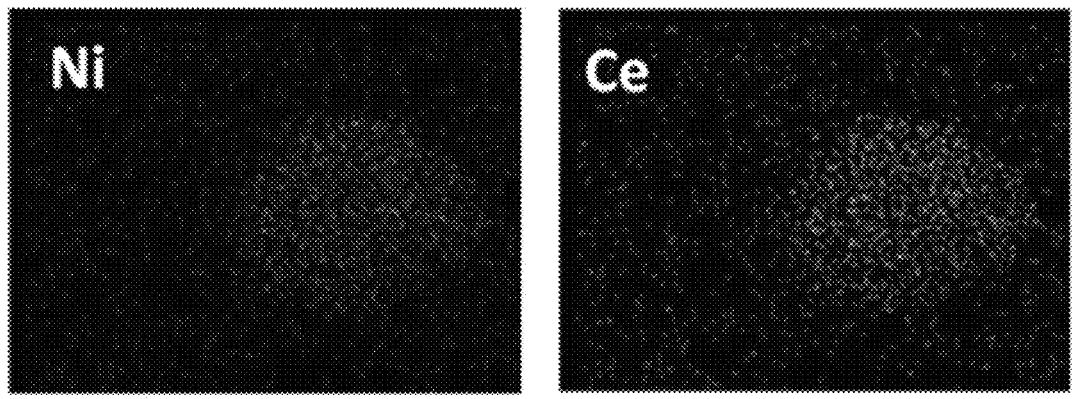
FIG. 3B is an EDS spectrum of Comparative Example 1.
Figure 4A:
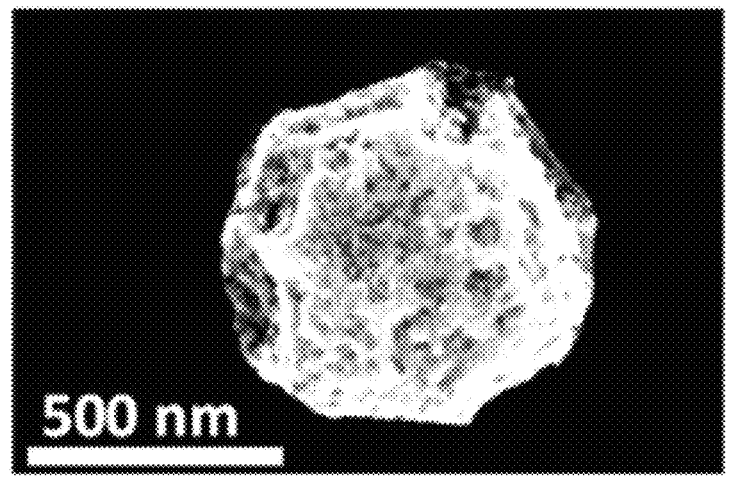
FIG. 4A is a FESEM image of Example 1.
Figure 4B:
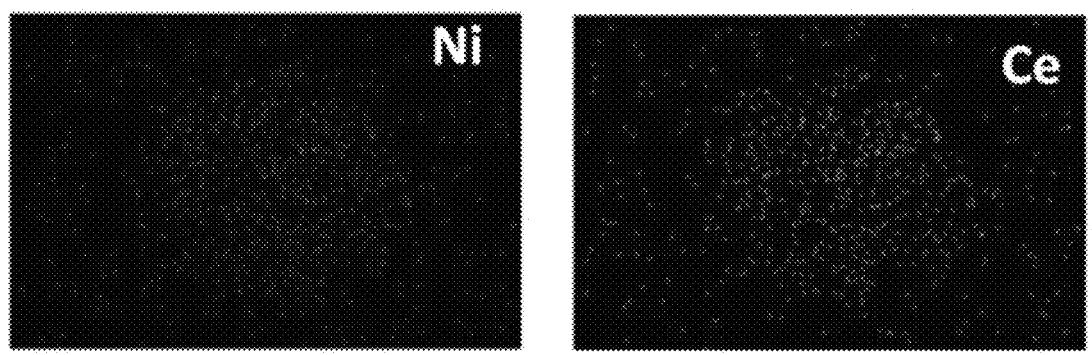
FIG. 4B is an EDS spectrum of Example 1.
Figure 4B:
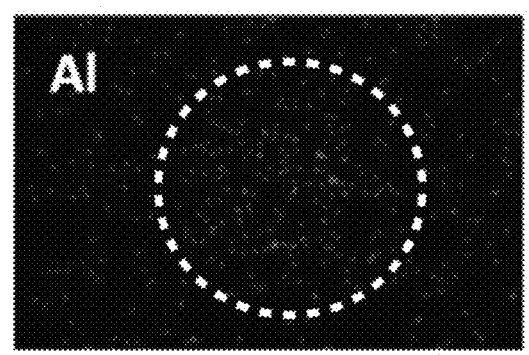

Please refer to FIGS. 3A, 3B, 4A and 4B, wherein FIG. 3A is a FESEM image of Comparative Example 1. FIG. 3B is an EDS spectrum of Comparative Example 1. FIG. 4A is a FESEM image of Example 1. FIG. 4B is an EDS spectrum of Example 1. As shown in FIG. 3A and FIG. 4A, the morphology of Comparative Example 1 and Example 1 are spherical. As shown in FIG. 3B and FIG. 4B, nickel and cerium dioxide of Comparative Example 1 and Example 1 are uniformly distributed on the nanostructure. The results indicate that the Ni—Ce—O interface is successfully produced in both of the nanostructures of Comparative Example 1 and Example 1. Furthermore, the structure of Example 1 is observed in FIG. 4B, indicating that a successful formation of $Al_2O_3$ nanoparticle cluster (NPC) as the support material of Ni and $CeO_2$ nanoparticle (NP) via the gas-phase EISA.

Figure 5:
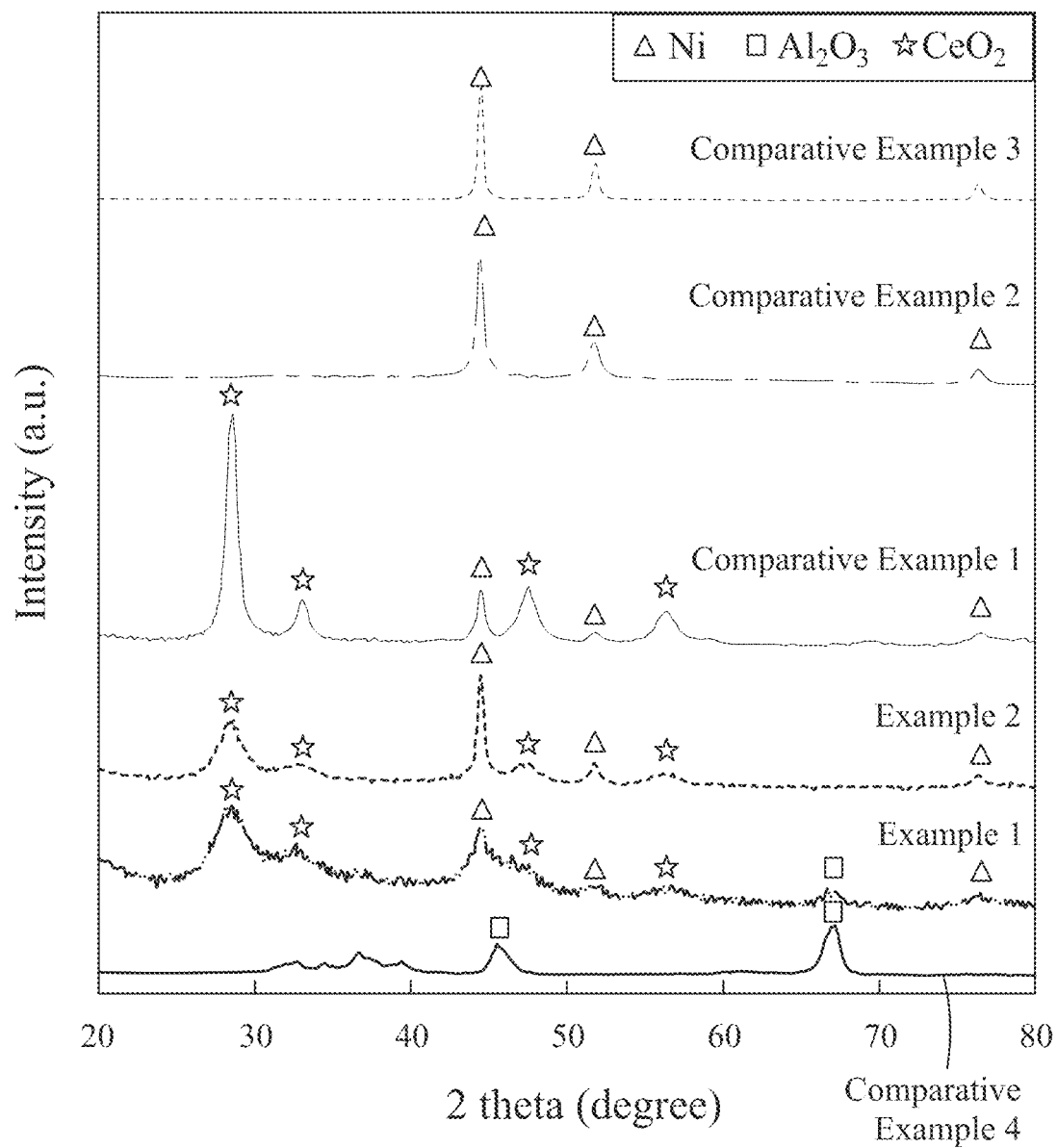
FIG. 5 is a XRD diffractogram of Example 1 to Example 2 and Comparative Example 1 to Comparative Example 4.

Please refer to FIG. 5, which is a XRD diffractogram of Example 1 to Example 2 and Comparative Example 1 to Comparative Example 4. As shown in FIG. 5, only the crystalline phase of metallic Ni is presented in Comparative Example 3, indicating that NiO is reduced to metallic Ni by hydrogen at the second calcining temperature. However, the crystalline phases of metallic Ni and $CeO_2$ are presented in Comparative Example 1, and the crystalline phases of metallic Ni, $CeO_2$ and $Al_2O_3$ are presented in Example 1. The results indicate that no matter whether aluminum oxide nanopowder is added to the precursor solution or not, NiO is reduced to metallic Ni by hydrogen selectively at the second calcining temperature, and $CeO_2$ and $Al_2O_3$ are not reduced by hydrogen at the second calcining temperature. Furthermore, the crystallite size of Ni ($d_{Ni}$) can be estimated by analyzing the waveform of the X-ray diffraction peak, and as shown in Table 2. The aforementioned results indicate that Example 1 has $Al_2O_3$ nanoparticle cluster, which can effectively reduce the crystallite size of nickel. The reason is that the $Al_2O_3$ nanoparticle cluster can improve the dispersibility of nickel and can inhibit the sintering of nickel at the first calcining step and the second calcining step.

TABLE 2

|  | $d_{Ni}$ (nm) |
| --- | --- |
| Example 1 | 6.80 |
| Example 2 | 15.6 |
| Comparative Example 1 | 14.3 |
| Comparative Example 2 | 17.0 |
| Comparative Example 3 | 21.3 |
| Comparative Example 4 | N/A |

Furthermore, the analysis of the specific surface area ($S_{BET}$), the metal surface area ($S_{msa}$) and the metal dispersion (D) of Example 1 to Example 2 and Comparative Example 1 to Comparative Example 4 are shown in Table 3. As shown in Table 3, in Comparative Example 3 with only nickel, the $S_{BET}$ and $S_{msa}$ of Comparative Example 3 are relatively low compared to other $CeO_2$ and/or $Al_2O_3$. In the precursor solution, at a constant $C_{ce}/C_{Ni}$ is 0.61 (Example 1, Example 2, Comparative Example 1), by increasing $C_{Al}/C_{Ni}$ from 0 to 0.31 and 1.56, $S_{BET}$ is increased from 55.8 m²/g to 74.9 m²/g and 101.9 m²/g, and $S_{msa}$ is increased from 2.8 m²/g to 3.7 m²/g and 10.9 m²/g simultaneously. The aforementioned results indicate that adding the nanostructure $CeO_2$ and/or $Al_2O_3$ can increase the surface area of the catalyst, which is attributed to the inhibition of the sintering of metallic Ni during the aerosol-based synthesis process (i.e., the first calcining step and the second calcining step). Therefore, both $CeO_2$ and $Al_2O_3$ are beneficial to improve the metal dispersion in the nanostructure.

TABLE 3

|  | $S_{BET}$ (m²/g) | $S_{msa}$ (m²/g) | D (%) |
| --- | --- | --- | --- |
| Example 1 | 101.9 | 10.9 | 7.28 |
| Example 2 | 74.9 | 3.7 | 1.16 |
| Comparative Example 1 | 55.8 | 2.8 | 0.69 |
| Comparative Example 2 | 67.8 | 6.3 | 1.24 |
| Comparative Example 3 | 32.6 | 0.1 | 0.02 |
| Comparative Example 4 | 95.6 | N/A | N/A |

Figure 6:
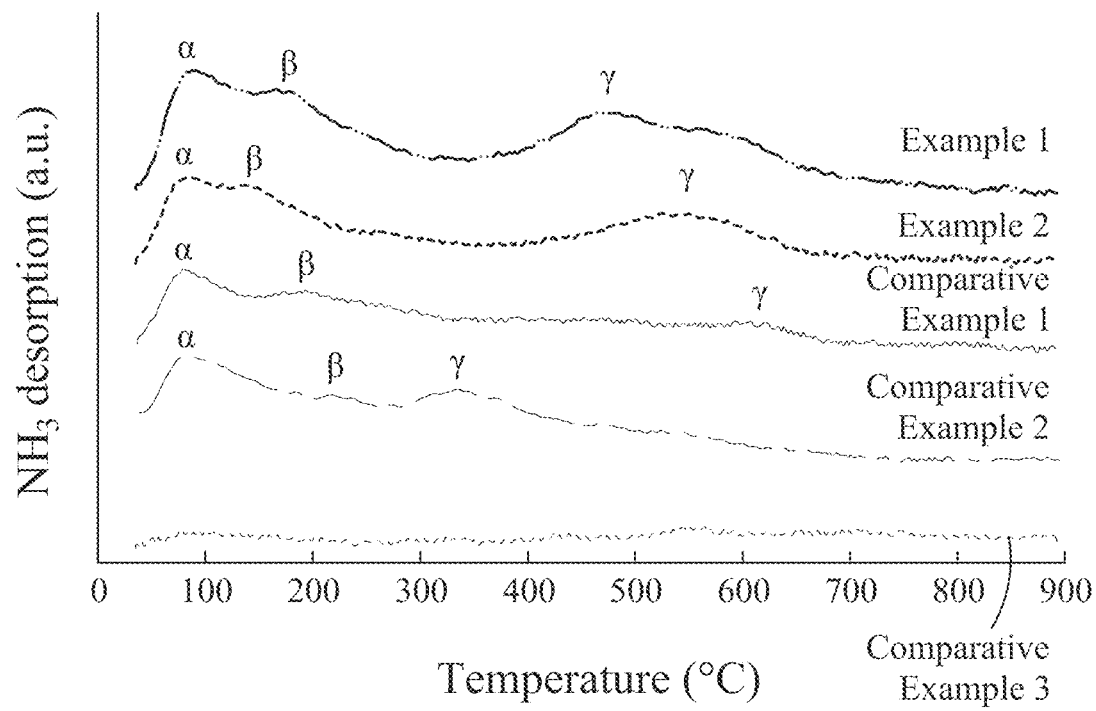
FIG. 6 is a NH3-TPD analysis of Example 1 to Example 2 and Comparative Example 1 to Comparative Example 3.

Please refer to FIG. 6, which is a $NH_3$-TPD analysis of Example 1 to Example 2 and Comparative Example 1 to Comparative Example 3. As shown in FIG. 6, except for Comparative Example 3, α, β and γ peaks are identified in Example 1, Example 2, Comparative Example 1 and Comparative Example 2. The α and β peaks are considered as the low acidic site, and the intensity of the peak are mainly correlated to the surface area of the catalyst. The γ peak is considered the relative high acidic site, and its peak temperature is strongly affected by the acidity of the catalyst surface. The aforementioned results indicate that the acidity of the Ni catalyst can be increased by having $CeO_2$ and/or $Al_2O_3$ nanoparticle cluster, and $CeO_2$ is more acidic than $Al_2O_3$ due to Comparative Example 1 has a higher peak temperature than Comparative Example 2. Furthermore, in the nickel-cerium dioxide-aluminum oxide hybrid nanoparticle cluster catalyst, the surface area of the catalyst is increased with the increase of $C_{Al}$, as evidenced by the peak areas of α, β and γ peaks. Noted that no distinct any peak is identified for Comparative Example 3 due to the low surface area.

2. Reductive Amination Reaction of Polypropylene Glycol

The nickel-cerium dioxide-aluminum oxide hybrid nanoparticle cluster catalyst of the present disclosure is performed the reductive amination reaction of polypropylene glycol step of the step 220 of the method for synthesizing polyetheramine 200 as shown in FIG. 2. In a 250 mL autoclave reaction system, the temperature is maintained at 230° C., the pressure is maintained at 10.34 MPa for 2 hours. Next, the feed is added, which includes 5 g polypropylene glycol (PPG), hydrogen and ammonia. The molar ratio of hydrogen to polypropylene glycol is 1.55, and the molar ratio of ammonia to polypropylene glycol is 40.6. Then, the product is heated at 130° C. of the oil bath under an atmospheric condition so as to remove water and unreacted ammonia.

Figure 7:
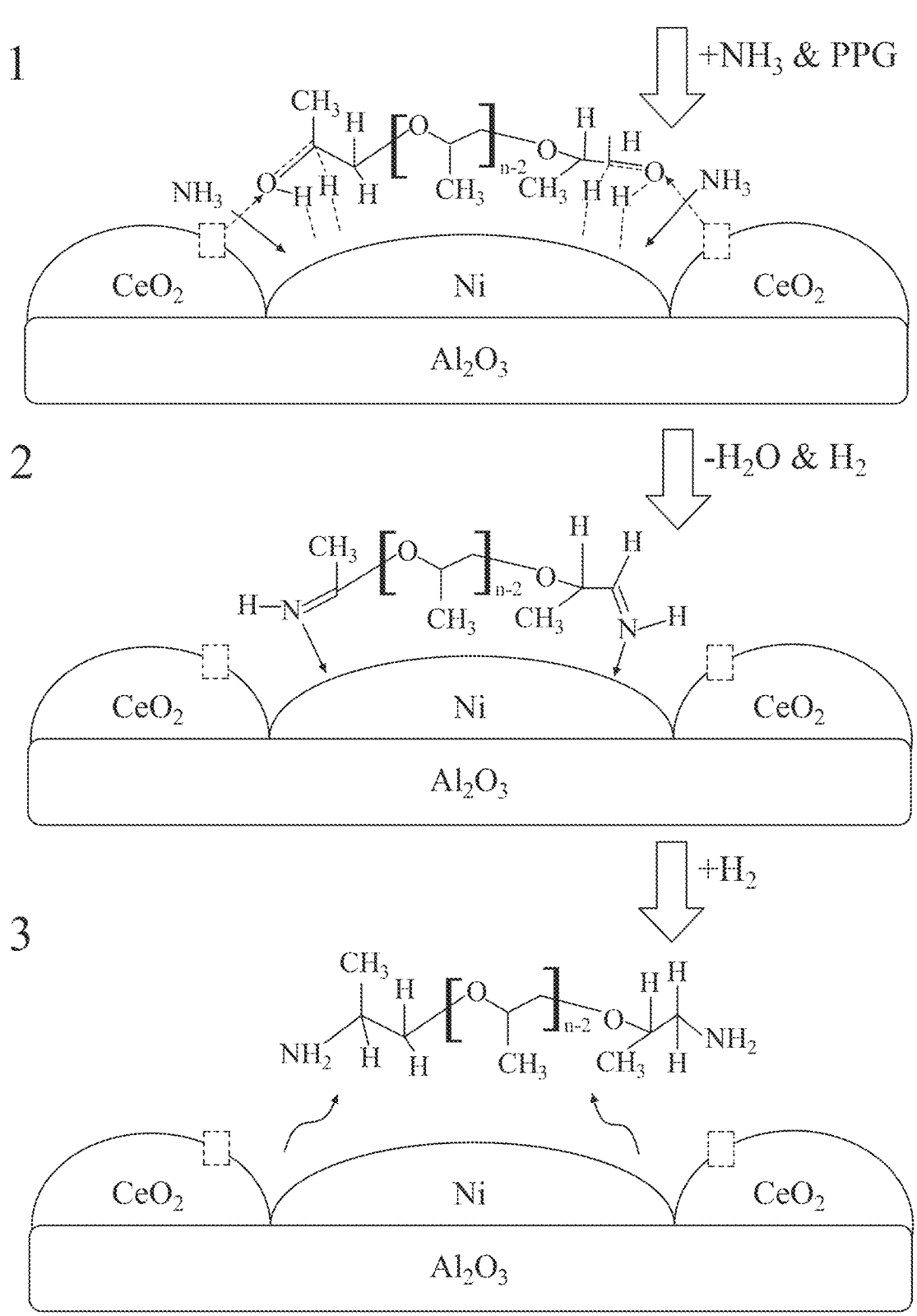
FIG. 7 is a schematic view for the reaction mechanism of the reductive amination reaction of polypropylene glycol catalyzed by the nickel-cerium dioxide-aluminum oxide hybrid nanoparticle cluster catalyst.

Please refer to FIG. 7, which is a schematic view for the reaction mechanism of the reductive amination reaction of polypropylene glycol catalyzed by the nickel-cerium dioxide-aluminum oxide hybrid nanoparticle cluster catalyst, and includes the steps 1 to 3. The step 1: PPG adsorbs to the surface of the nickel-cerium dioxide-aluminum oxide hybrid nanoparticle cluster catalyst, and ammonia simultaneously adsorbs to the surface of Ni. The step 2: PPG interacts with oxygen vacancy on the surface of $CeO_2$ to promote the dehydrogenation at the interface of Ni—$CeO_2$, and after the condensation reaction, the dehydrogenated PPG reacts with liquid ammonia to form polyimine. The step 3: polyimine reacts with the adsorbed hydrogen to form polyetheramine, and polyetheramine is desorbed from the surface of Ni. Here, the interface of Ni—Ce—O provides the additional active sites for the dehydrogenation of PPG, which will reduce the impact of the strong competitive adsorption of ammonia at the surface of Ni with PPG. Besides, the desorption of polyetheramine is enhanced by $CeO_2$, and $CeO_2$ also inhibits the formation of $Ni_3N$ on the surface of Ni.

Figure 8:
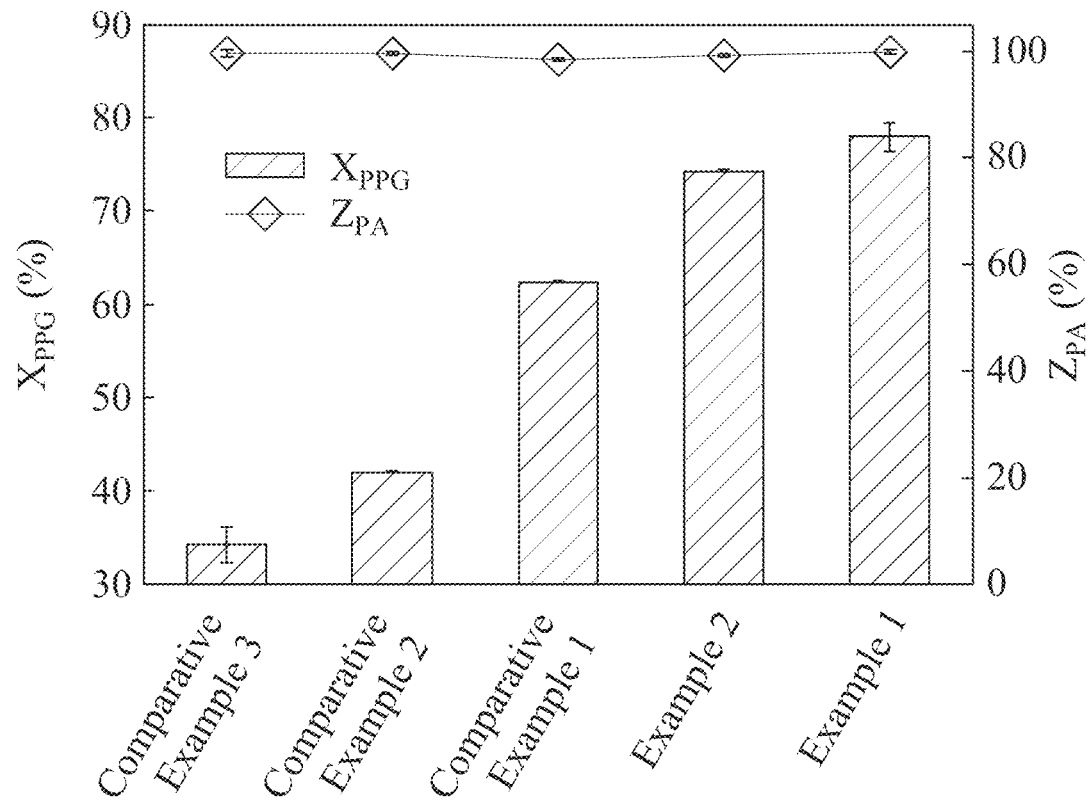
FIG. 8 is a histogram for the conversion ratio of PPG and the selectivity to primary amine of Example 1 to Example 2 and Comparative Example 1 to Comparative Example 3.

3. The Activity Test of the Nickel-Cerium Dioxide-Aluminum Oxide Hybrid Nanoparticle Cluster Catalyst Please refer to FIG. 8, which is a histogram for the conversion ratio of PPG ($X_{PPG}$) and the selectivity to primary amine ($Z_{PA}$) of Example 1 to Example 2 and Comparative Example 1 to Comparative Example 3. As shown in FIG. 8, $X_{PPG}$ of Comparative Example 3 only containing nickel catalyst is 34.3%. $X_{PPG}$ of Comparative Example 2 after adding $Al_2O_3$ nanoparticle cluster is increased to 42.0%. $X_{PPG}$ of Comparative Example 1 after adding $CeO_2$ is increased to 62.3%. Furthermore, in the precursor solution, at a constant $C_{ce}/C_{Ni}$ is 0.61, by increasing $C_{Al}/C_{Ni}$ from 0 to 0.31 and 1.56, $X_{PPG}$ is increased from 62.3% to 74.2% and 77.9%. The aforementioned results indicate that adding $CeO_2$ and $Al_2O_3$ nanoparticle cluster to Ni catalyst can increase the activity of the catalyst, and is directly proportional to CAI. The selectivity to primary amine ($Z_{PA}$) of Example 1 to Example 2 and Comparative Example 1 to Comparative Example 3 are as high as 98.5% to 99.7%.

Figure 9:
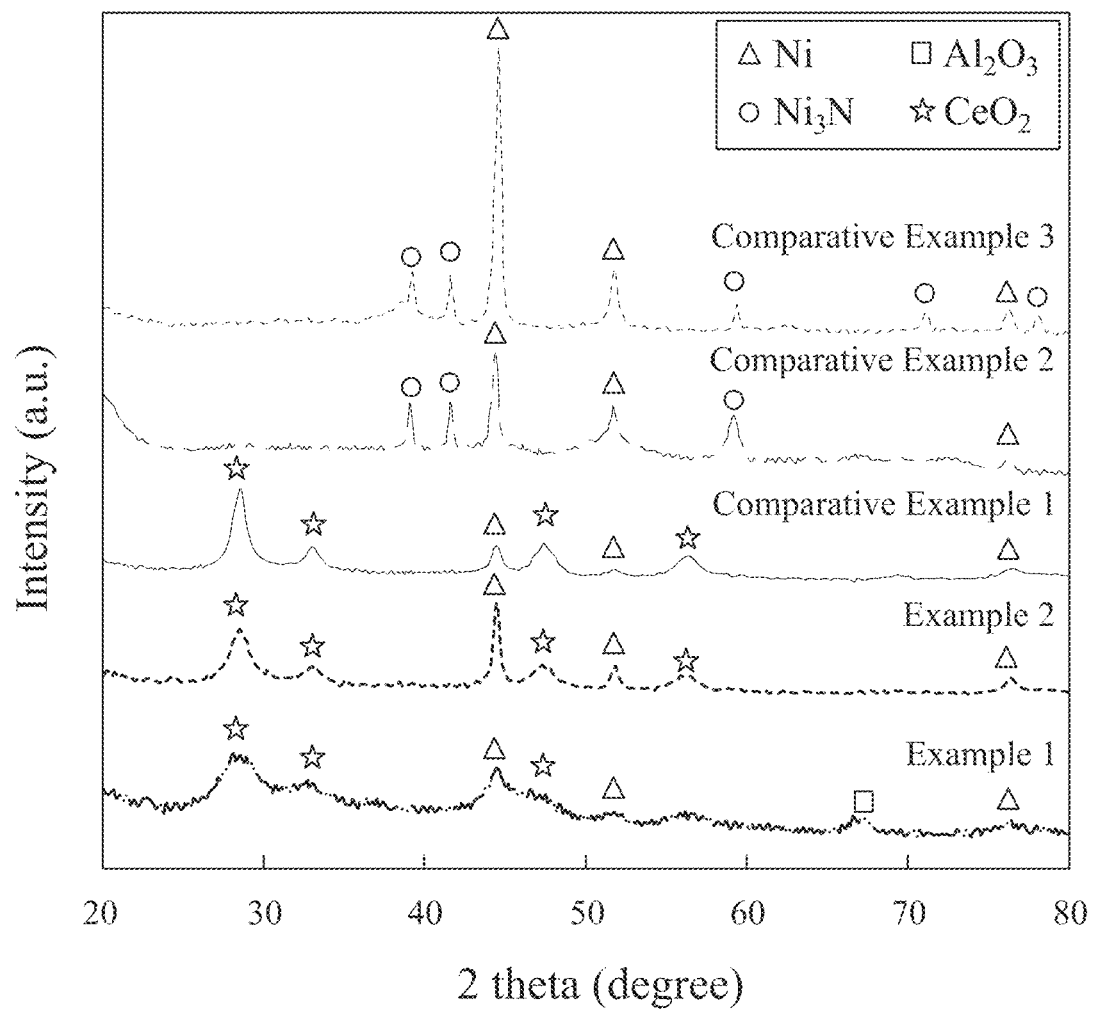
FIG. 9 is an XRD diffractogram of Example 1 to Example 2 and Comparative Example 1 to Comparative Example 3 after the reductive amination reaction.

4. The Stability Test of the Nickel-Cerium Dioxide-Aluminum Oxide Hybrid Nanoparticle Cluster Catalyst Please refer to FIG. 9, which is an XRD diffractogram of Example 1 to Example 2 and Comparative Example 1 to Comparative Example 3 after the reductive amination reaction. As shown in FIG. 9, after the reductive amination reaction, only the crystalline phase of metallic Ni is identified, indicating that the amount of oxidized Ni is insignificant. Furthermore, the crystallite size of Ni ($d_{Ni}$) can be estimated by analyzing the waveform of the X-ray diffraction peak, and compared with the crystallite size before the reductive amination reaction. As shown in Table 4, the crystallite size of Ni of the catalyst before the reductive amination reaction and after the reductive amination reaction do not change significantly, indicating that the sintering of Ni can be negligible during the catalysis.

TABLE 4

|  | before the reductive amination reaction $d_{Ni}$ (nm) | after the reductive amination reaction $d_{Ni}$ (nm) |
| --- | --- | --- |
| Example 1 | 6.8 | 6.3 |
| Example 2 | 15.6 | 14.4 |
| Comparative Example 1 | 14.3 | 15.1 |
| Comparative Example 2 | 17.0 | 20.7 |
| Comparative Example 3 | 21.3 | 21.6 |

Furthermore, in FIG. 9, the crystalline phase of $Ni_3N$ is presented in Comparative Example 2 and Comparative Example 3, which is attributed to the strong adsorption of ammonia on the metal surface especially in a hydrogen-deficient condition, and during the reaction, the nitridation reaction is considered as a catalyst deactivation pathway. In contrast, the crystalline phase of $Ni_3N$ is unable to clearly identify in Example 1, Example 2 and Comparative Example 1, indicating that the addition of $CeO_2$ will inhibit the formation of $Ni_3N$.

Figure 10A:
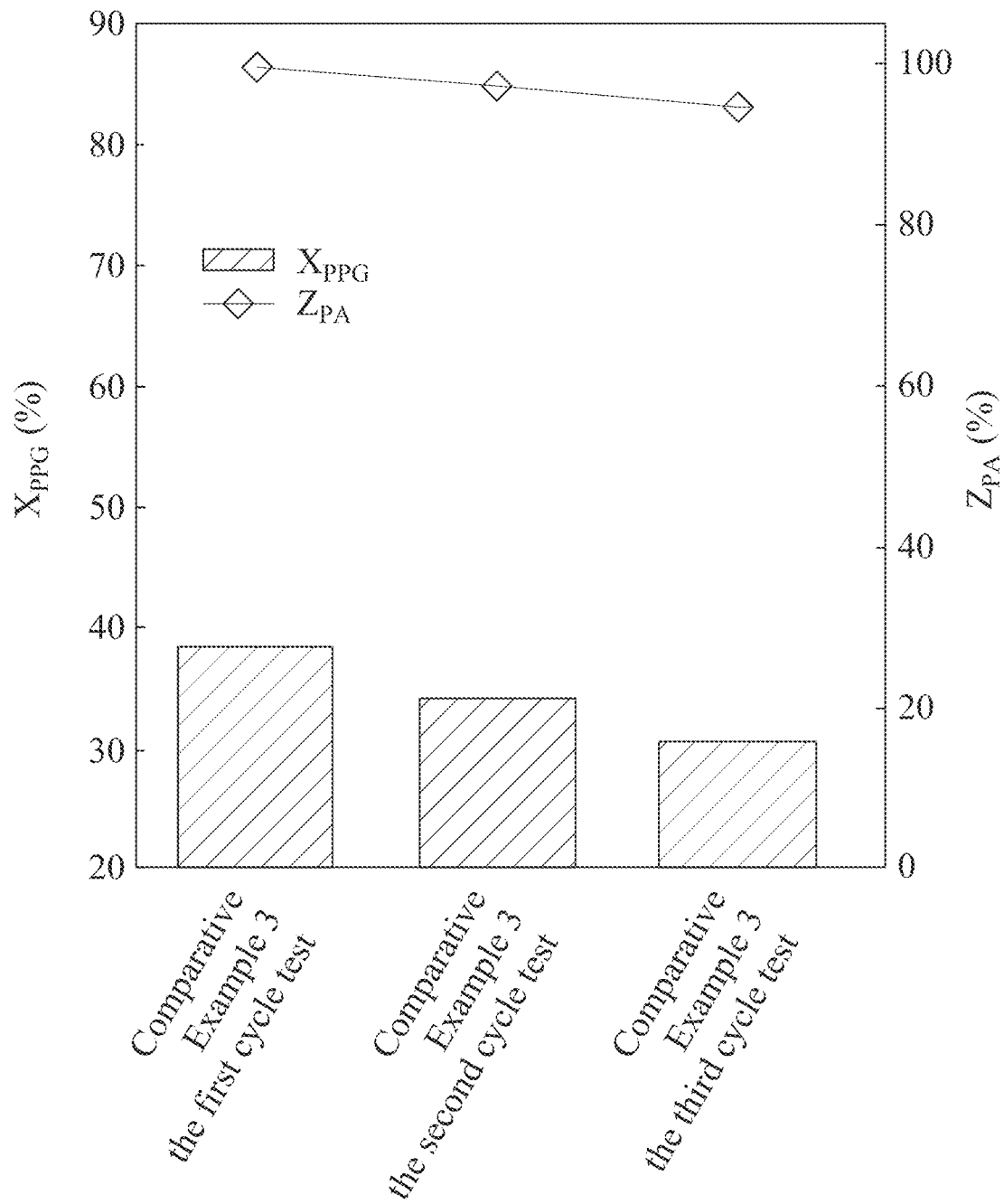
FIG. 10 A is a histogram for the conversion ratio of PPG and the selectivity to primary amine from the first, the second and the third cycle tests according to Comparative Example 3 of the present disclosure.
FIG. 10B is a histogram for the conversion ratio of PPG and the selectivity to primary amine from the first, the second and the third cycle tests according to Example 1 of the present disclosure.
Figure 10B:
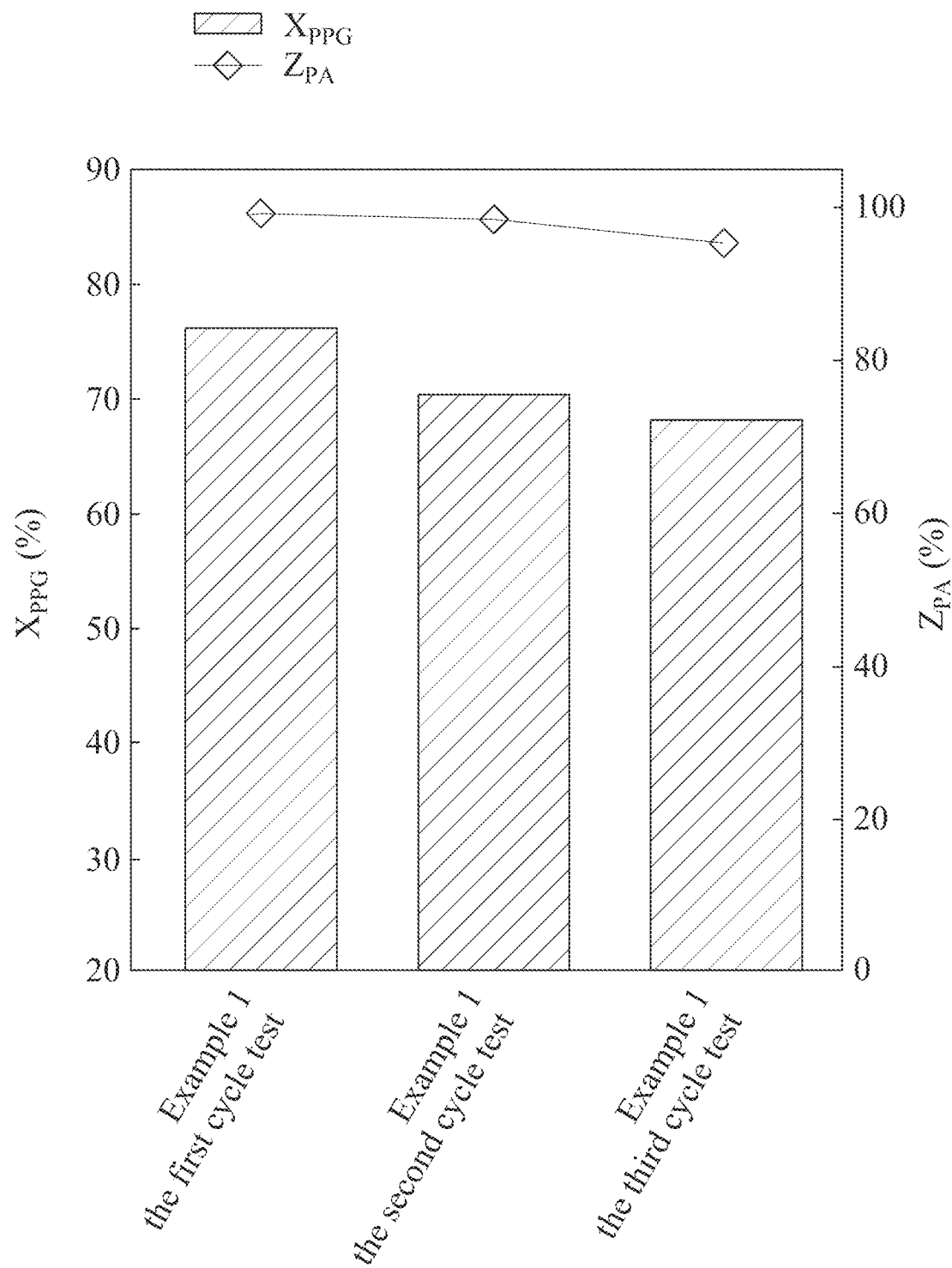

Please refer to FIG. 10A and FIG. 10B, wherein FIG. 10A is a histogram for the conversion ratio of PPG and the selectivity to primary amine from the first, the second and the third cycle tests according to Comparative Example 3 of the present disclosure. FIG. 10B is a histogram for the conversion ratio of PPG and the selectivity to primary amine from the first, the second and the third cycle tests according to Example 1 of the present disclosure. As shown in FIG. 10A, $X_{PPG}$ of Comparative Example 3 is 34.2% after the second cycle test and 30.7% after the third cycle test, which is 11.2% and 20.3% lower than that of the first cycle test, respectively. In comparison, in the three cycle tests, $X_{PPG}$ of Example 1 is higher than that of Comparative Example 3, wherein $X_{PPG}$ of Example 1 is 70.3% after the second cycle test and 68.0% after the third cycle test, which is 7.7% and 10.8% lower than that of the first cycle test, respectively. The results indicate that the addition of $CeO_2$ and $Al_2O_3$ nanoparticle cluster will improve the stability of the Ni catalyst to catalyze the reductive amination reaction of the polypropylene glycol, and the stability is improved by adding $CeO_2$ to inhibit the formation of $Ni_3N$ and the sintering of the crystalline phase of metallic Ni.

Furthermore, in FIG. 10A and FIG. 10B, $Z_{PA}$ is shown to slightly decrease over the three cycle tests. For Comparative Example 3, $Z_{PA}$ is decreased to 97.3% and 94.6% after the second cycle test and the third cycle test, respectively. For Example 1, $Z_{P4}$ is decreased to 98.4% and 95.4% after the second cycle test and the third cycle test, respectively. The results indicate that the decline of $Z_{P4}$ is attributed to the adsorbed product after the first cycle test turning to be further aminated in the following second and third cycle tests.

In conclusion, the nickel-cerium dioxide-aluminum oxide hybrid nanoparticle cluster catalyst of the present disclosure is synthesized by the aerosol process, with the $Al_2O_3$ nanoparticle cluster as the support and $CeO_2$ as the co-catalyst. The active surface area of the catalyst is increased by the special aluminum oxide nanoparticle cluster structure, and the addition of the $CeO_2$ co-catalyst provides a good interface metal-support effect, so that the concerted reaction occurred at the interface can improve the activity, the stability and the selectivity of the catalyst. When the nickel-cerium dioxide-aluminum oxide hybrid nanoparticle cluster catalyst used as the catalyst for the reductive amination reaction of polypropylene glycol, the special aluminum oxide nanoparticle cluster structure can greatly improve the conversion ratio of PPG, and also has the high selectivity to primary amine. Furthermore, the nickel-cerium dioxide-aluminum oxide hybrid nanoparticle cluster catalyst still has high activity after repeated use, so that can improve the disadvantages of the catalyst obtained by the traditional processes and reduce the pollution.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A method for fabricating a nickel-cerium dioxide-aluminum oxide hybrid nanoparticle cluster catalyst, comprising:
    performing a solution preparation step, wherein a catalytically active precursor and a supporter precursor are mixed to obtain a precursor solution, the catalytically active precursor contains a nickel ion and a cerium ion, the supporter precursor contains an aluminum ion, and pH value of the precursor solution is 2.5 to 4;
    performing an aerosolizing step, wherein the precursor solution is aerosolized to obtain an atomized droplet;
    performing a drying step, wherein the atomized droplet is converted to a precursor crystallite by evaporation-induced self-assembly;
    performing a first calcining step, wherein the precursor crystallite is calcined to obtain an oxidation state catalyst;
    performing a reducing gas adding step, wherein hydrogen is added as a reducing gas; and
    performing a second calcining step, wherein the oxidation state catalyst is calcined to obtain the nickel-cerium dioxide-aluminum oxide hybrid nanoparticle cluster catalyst.

2. The method for fabricating the nickel-cerium dioxide-aluminum oxide hybrid nanoparticle cluster catalyst of claim 1, wherein the catalytically active precursor is a mixed solution of nickel nitrate and cerium nitrate.

3. The method for fabricating the nickel-cerium dioxide-aluminum oxide hybrid nanoparticle cluster catalyst of claim 1, wherein the support precursor is aluminum oxide nano-powder.

4. The method for fabricating the nickel-cerium dioxide-aluminum oxide hybrid nanoparticle cluster catalyst of claim 1, wherein a temperature of the first calcining step ranges from 400° C. to 700° C.

5. The method for fabricating the nickel-cerium dioxide-aluminum oxide hybrid nanoparticle cluster catalyst of claim 1, wherein a temperature of the second calcining step ranges from 600° C. to 800° C.

6. The method for fabricating the nickel-cerium dioxide-aluminum oxide hybrid nanoparticle cluster catalyst of claim 1, wherein in the precursor solution, an atomic ratio of cerium to nickel is 0.5 to 0.8.

7. The method for fabricating the nickel-cerium dioxide-aluminum oxide hybrid nanoparticle cluster catalyst of claim 6, wherein in the precursor solution, the atomic ratio of cerium to nickel is 0.61.

8. The method for fabricating the nickel-cerium dioxide-aluminum oxide hybrid nanoparticle cluster catalyst of claim 1, wherein in the precursor solution, an atomic ratio of aluminum to nickel is 0.3 to 1.8.

* * * * *